United States Patent [19]
Giordano et al.

[11] Patent Number: 5,897,696
[45] Date of Patent: Apr. 27, 1999

[54] RADIO-OPAQUE PAINT FOR MEDICAL STENTS

[75] Inventors: Russell A. Giordano, Sudbury, Mass.; Kevin C. Kopp, Burr Ridge, Ill.

[73] Assignees: Boston University, Boston, Mass.; Illinois University, Chicago, Ill.

[21] Appl. No.: 08/801,122

[22] Filed: Feb. 14, 1997

Related U.S. Application Data

[60] Provisional application No. 60/011,793, Feb. 16, 1996.

[51] Int. Cl.$^6$ .................................................. G21F 1/10
[52] U.S. Cl. ...................... 106/35; 252/478; 106/461; 106/471; 106/187.1; 106/181.1; 106/192.1; 106/194.2; 106/194.1; 106/198.1; 106/287.23; 106/287.24; 106/287.35
[58] Field of Search ..................... 252/478; 106/461, 106/471, 187.1, 181.1, 192.1, 194.2, 194.1, 198.1, 287.23, 287.24, 287.35, 35

[56] References Cited

U.S. PATENT DOCUMENTS

| | | | |
|---|---|---|---|
| 4,302,376 | 11/1981 | Walkowiak et al. | 106/35 |
| 4,866,132 | 9/1989 | Obligin et al. | 525/107 |
| 4,935,019 | 6/1990 | Papp, Jr. | 604/362 |
| 4,977,197 | 12/1990 | Sasaki et al. | 522/14 |
| 5,024,232 | 6/1991 | Smid et al. | 128/654 |
| 5,133,660 | 7/1992 | Fenick | 433/76 |
| 5,171,572 | 12/1992 | Sugasawa et al. | 106/461 |
| 5,204,383 | 4/1993 | Manabe et al. | 523/118 |
| 5,256,334 | 10/1993 | Smid et al. | 252/478 |
| 5,334,625 | 8/1994 | Ibsen et al. | 523/113 |
| 5,415,546 | 5/1995 | Cox, Sr. | 433/213 |

FOREIGN PATENT DOCUMENTS

| | | |
|---|---|---|
| 0272901 | 6/1988 | European Pat. Off. . |
| 9005554 | 5/1990 | WIPO . |

OTHER PUBLICATIONS

H. Israelson et al., Barium–Coated Surgical Stents and Computer–Assisted Tomography in the Preoperative Assessment of Dental Implant Patents, *The International Journal of Periodontics & Restorative Dentistry*, 1992, Vol. 12, No. 1, pp. 52–61.

Effective Uses of Radiographs for Implant Placements—Panographs, Cephalograms, CT Scans, *Dental Implantology Update*, Apr. 1993, vol. 4, No. 4.

Interactive Radiologic Diagnosis and Case Planning for Implants, *Dental Implantology Update*, Apr. 1993, vol. 5, No. 7, pp. 49–55.

*Primary Examiner*—Melissa Bonner
*Attorney, Agent, or Firm*—Samuels, Gauthier & Stevens

[57] ABSTRACT

A process for preparing a water-soluble, radio-opaque paint for marking acrylic resin dental stents includes the steps of preparing a solution comprising 50 ml of ethanol, 6.4 grams of glycerol; 4.0 ml of benzaldehyde; 1.0 ml of glacial acetic acid, and 0.15 grams of hydroxy propyl cellulose. A radio-opaque powder, such as 50 grams of barium sulfate powder having a mean particle diameter of about 10 $\mu$m, is then added to the solution. The solution is then mixed to obtain the paint, wherein the paint has a uniform dispersion of the radio-opaque powder. This paint may be used on dental stents to locate and guide placement of dental implants. The method may include the steps of preparing a water-soluble, radio-opaque paint for marking dental stents comprising the steps of preparing a solution described above; adding a radio-opaque powder, such as 50 grams of barium sulfate powder; and mixing the solution to obtain the paint, wherein the paint has a uniform dispersion of the radio-opaque powder. The uniform dispersion may be obtained by using ultrasound. Further, the method comprises applying the paint to a dental stent; placing the stent in contact with a patient's teeth; taking a radiographic image of the stent and the patient's teeth. The stent then is removed from the patient's teeth, and the paint is removed from the stent.

17 Claims, 7 Drawing Sheets

RADIO-OPAQUE PAINT FOR MEDICAL STENTS

This application claims priority from Provisional application Ser. No. 06/011,793 filed Feb. 16, 1996.

BACKGROUND

1. Field of the Invention

The invention relates to the fabrication of a durable, but water soluble; non-toxic coating which may be applied to and removed from radio-lucent medical stents. In particular, this coating allows the radiographic imaging of the stents mounted on teeth in a patient's mouth, and such stents may be used to position and to guide the placement of dental implants.

2. Description of the Related Art

The placement of an implant-retained dental restoration in a patient's mouth is a complicated, multi-step process. In order to anchor the restoration in the patient's mouth, a dental implant is placed into the patient's jaw or skull. This implant provides an anchoring device for the abutment and screw which will eventually secure the restoration, e.g., a replacement tooth or bridge. However, it often is difficult to locate sufficient maxillary (sinus) or mandibular (jaw) bone within which to fix the implant, so that an adequate foundation and proper positioning of the restoration may be achieved. Because the underlying bone structure and its density or mass may not be readily apparent on radiographs, implants may inadvertently be positioned in bone structure of insufficient density or mass to form a proper foundation for the implant. This may ultimately lead to the implant's failure. In addition, an implant seated at an improper angle may have an unaesthetic appearance, and an improperly seated implant may result in a malocclusion. Preoperative radiographic evaluations, such as conventional radiographs, X-ray images, CAT-scans, and the like, are used in combination with dental (or medical) stents to determine the proper site and angle of implantation.

The orientation of dental implants is usually governed by the existing anatomy and the desired position of the restoration(s). Once a functionally and esthetically desirable implant location has been identified, stents are fabricated to allow preferred positioning of the implant in the underlying bone. At the time of surgery, the anatomic information obtained from the radiographic evaluation is correlated with the desired implant location, as indicated by the stent, to position the implant at the preferred location and orientation. However, it is desirable to correlate the information obtained from the radiographic evaluation and the stent prior to surgery.

The stent is placed in a patient's mouth and is aligned with the location at which an implant is to be placed. A radiographic image is taken of the patient's mouth showing the position of the stent. By examining the radiographic image, a dentist, oral surgeon, or periodontist may determine whether sufficient bone exists under the stent to support the implant. If insufficient bone is present, additional bone may be grafted to the patient's sinus or jaw, a different location for the periodontal implant may be chosen, or a different mode of treatment eliminating the use of an implant may be selected. If sufficient bone is present, however, the stent may later be used to guide the placement of the implant. The stent may either be transparent or translucent and may have guide holes or slots through which the implant may be positioned. Thus, stents preferably possess two qualities: (1) they are radiographically opaque and (2) they are visually translucent or transparent.

Stents may be fabricated by technicians from an acrylic resin. However, acrylic resin is radio-lucent, i.e., not radio-opaque. The stent may be made radio-opaque by the addition of a radio-opaque powder, such as barium sulfate powder, to the acrylic resin during the fabrication of the stent. Many procedures or recipes for preparing stents containing barium sulfate are possible and are used. Generally, however, technicians simply mix a quantity of radio-opaque powder into the acrylic resin base. Such powders are readily available from medical and dental laboratory supply companies. Although, barium sulfate is a frequently used radio-opaque powder, other radio-opaque powders, such as metal powders, also are used. Nevertheless, metal powders or metal flakes tend to reflect or deflect the X-rays, which may cause unsatisfactory radiographs and uncontrolled or blurred exposure.

The lack of a standardized procedure or recipe, however, is a disadvantage of the current methods of fabricating radio-opaque stents. Unless the barium sulfate powder is added in the proper quantity and is thoroughly mixed in the acrylic material, the opacity of the stent may be uneven. Further, settling may occur during the hardening of the acrylic, which may create additional unevenness in the opacity. If the stent is not uniformly radio-opaque, it may be difficult to properly locate the position for the proposed implant. Therefore, existing radio-opaque medical stents may not provide an accurate determination of proper drilling angles for positioning of implants and may create distortion in the radiographs, for example, due to the presence of metallic powders or flakes.

SUMMARY OF THE INVENTION

Thus, the need has arisen for providing a radio-opaque paint which may be applied to a radio-lucent stent sculpted or molded in shape to aid in the determination of drilling angles for implant placement on radiographs, and at the same time allow for adjustments based upon occlusal surface angles and peculiarities of tooth confirmation. Preferredly, such a stent is tooth-shaped and is made of a material which may easily be sculpted or modified in shape after it is molded, so that it may serve not only as a radio-opaque stent for determination of drilling angles on a radiograph, such as conventional radiographs, X-ray images, CAT-scans, and the like, but also as an accurate indicator of the final anatomical from and shape of the restoration. This latter advantage allows dentists, oral surgeons, and periodontists, and the like, to determine not only the proper angles for drilling with respect to the underlying bone structure, but also to take into account any peculiarities in the tooth shape, which might require the adjustment of those angles for the final implant placement process. Further, a need has arisen for a water soluble radio-opaque paint which may be easily removed from the stent after use. In addition, although the paint is water soluble, it is preferably comprised of non-toxic components, such that any portion of the paint which may dissolve in a patient's mouth and may be ingested is not harmful to the patient, and such that the paint may be readily (and repeatedly, if necessary) reapplied to ensure complete radio-opaque coverage of the stent.

In an embodiment, the invention is a process for preparing a water-soluble, radio-opaque paint for marking radio-lucent medical, e.g., dental, stents. The process may comprise the steps of preparing a solution comprising a polar solvent, such as ethanol, methanol, isopropanol, and the like; a liquid adhesion thickener, such as glycerin and glycerol; a preservative, such as benzaldehyde; a food grade acidulant; and a dispersion stabilizer, such as a material selected from the cellulose family. For example, suitable food grade acidulants may include acetic acid, benzoic acid, citric acid, formic acid, lactic acid, malic acid, phosphoric acid, tartaric acid, and the like. The food grade acidulant may be added in an amount (and in a concentration) sufficient to alter the pH of the paint to a range of about 5.0 to 6.5. Similarly, the cellulose family of dispersion stabilizers may include hydroxy propyl cellulose, methyl cellulose, ethyl cellulose, and the like. A radio-opaque powder then is added to the solution. The solution is then mixed to obtain the paint, wherein the paint has a uniform dispersion of the radio-opaque powder.

In another embodiment, the invention is a method for using radio-lucent medical stents to locate and guide placement of surgical implants. The method may comprise the steps of preparing a water-soluble, radio-opaque paint for marking surgical stents. The method may further comprise the steps of preparing a solution comprising a polar solvent, a liquid adhesion thickener, a preservative, a food grade acidulant, and a dispersion stabilizer; adding a radio-opaque powder; and mixing the solution to obtain the paint, wherein the paint has a uniform dispersion of the radio-opaque powder. The uniform dispersion may be obtained by using ultrasound, e.g., sound with a frequency in a range greater than about 20,000 cycles per minute (cpm). In addition, the method may comprise applying the paint to a medical stent; placing the stent in contact with a portion of a patient's body; and taking a radiographic image of the stent and the portion of the patient's body. The stent then may be removed from contact with the portion of the patient's body, and the paint may be removed from the stent, e.g., by washing the stent with water and a detergent.

It is a technical advantage of this invention that the paint may be applied to the exterior of the stent by painting or spraying. Consequently, if a uniform coating is not initially applied to the stent, additional paint may be applied after non-radio-opaque areas have been identified. Moreover, the paint may be used in conjunction with known stents fabricated from acrylic resins containing barium sulfate. If an acrylic stent is prepared by known methods and non-radio-opaque areas are discovered, the paint of this invention may be used to cover, e.g., touch-up, these non-radio-opaque areas.

In addition, it is a technical advantage that the paint is water-soluble and, thus, may dissolve in water over time or may be removed through the use of water and soap or detergent. The elements of the solution may be food additives and, in the quantities applied with respect to the use of the invention, are not toxic to patients. Further, barium sulfate is a radio-opaque compound used in various medical procedures, such as a barium (sulfate) enema. Therefore, in the quantities and manner used in the invention, barium sulfate is generally not toxic to patients. However, in order to place the stent and obtain a suitable radiograph, preferably, the paint remains substantially undissolved for at least about 30 minutes. As noted above, however, one technical advantage of the paint is that it may be reapplied to areas at which excessive thinning or dissolving has occurred.

Other objects, features, and technical advantages will be apparent to persons skilled in the art in view of the following detailed description and the accompanying drawings and radiographs.

BRIEF DESCRIPTION OF THE DRAWINGS

For a more complete understanding of the present invention, and the technical advantages thereof, reference is now made to the following detailed description taken in conjunction with the accompanying drawings and radiographs.

FIG. 9b is a cross-sectional (or sagittal) view of the patient's mandible of FIG. 7, taken along the Line IXb—IXb above the cross-sectional (or sagittal) view depicted in FIG. 9a.

DETAILED DESCRIPTION OF PREFERRED EMBODIMENTS

According to the present invention, a process for preparing a water-soluble, radio-opaque paint for marking radio-lucent dental stents may include the step of preparing a solution comprising about 50 ml of ethanol; about 6.4 grams of glycerol; about 4.0 ml of benzaldehyde; about 10 ml of glacial (100%) acetic acid; and about 0.15 grams of hydroxy propyl cellulose. A measured amount of a radio-opaque powder, such as about 50 grams of barium sulfate, then is added to the solution. Suitable barium sulfate powder is commercially available and has a mean particle diameter of less than about 10 $\mu$m. If sufficiently fine barium sulfate powder is not available, less fine powder may be ball milled in deionized water until suitable mean particle diameters are obtained. For example, to achieve a mean particle diameter of less than about 10 $\mu$m, barium sulfate may be ball milled in deionized water for about 24 hours, filtered, and then dried for about 48 hours at about 60° C. This solution then is mixed to obtain the paint, such that the paint has a uniform dispersion of the radio-opaque powder.

This paint may be used on dental stents to locate and guide placement and to ensure proper orientation of dental implants. The uniform dispersion of the powder throughout the solution may be achieved by using ultrasound. For example, the uniform dispersion may be obtained by subjecting the combination of the solution and the radio-opaque powder to sonification at a frequency in a range greater than about 20,000 cpm. The method of using the paint comprises applying the paint to a dental stent; placing the stent on a patient's remaining teeth; and taking a radiographic image of the stent and the patient's teeth. The paint may be applied by various means including brushes, swabs, sponges, and spray, e.g., aerosol spray, applicators.

If the boundaries or edges of the stent are not clearly visible on radiographs or if markers deliberately painted on the stent by a dentist, oral surgeon, or periodontist are not sufficiently distinct for purposes of placing or orienting dental implants, the stent may be removed, and additional paint may be applied to the boundaries or edges of the stent or to the markers. After sufficiently clear, e.g., delimiting and distinct, radiographs are obtained, the stent may be removed from the patient's teeth, and the paint may be removed from the stent. Because the paint is water-soluble, the paint may be removed, for example, by scrubbing the stent with water or with a combination of water and a detergent.

Figure 1:
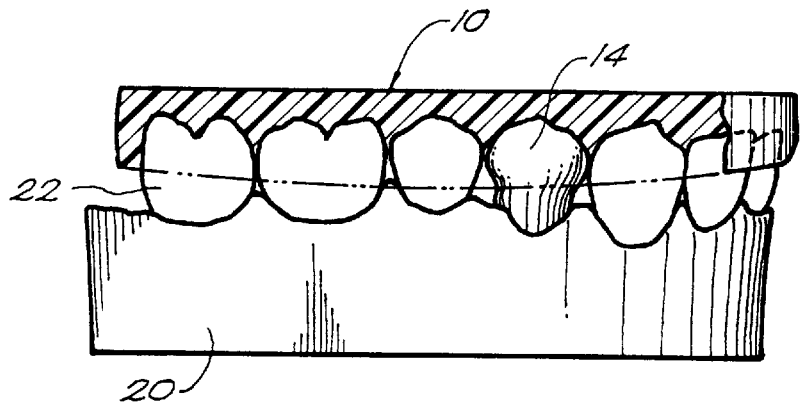
FIG. 1 depicts a stent mounted on a patient's teeth and including a restoration.
Figure 2:
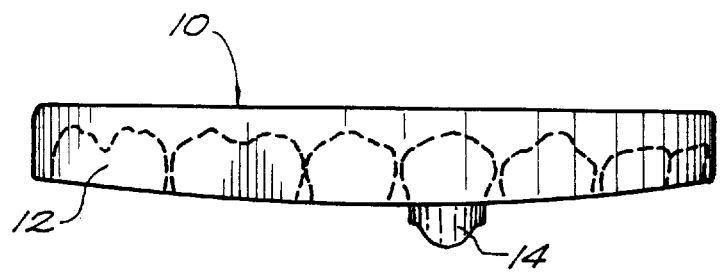
FIG. 2 depicts the stent of FIG. 1 holding a restoration and revealing tooth-shaped molds which conform to a patient's teeth.

Referring to FIG. 1, a stent 10 including a restoration 14 is depicted mounted on a patient's teeth 22, so that it does not cover the patient's gums 20 or obscure the gum line 20'. FIG. 2 depicts stent 10 of FIG. 1 holding restoration 14 and revealing a plurality of tooth-shaped molds 12 which conform to the patient's teeth 22.

Figure 3:
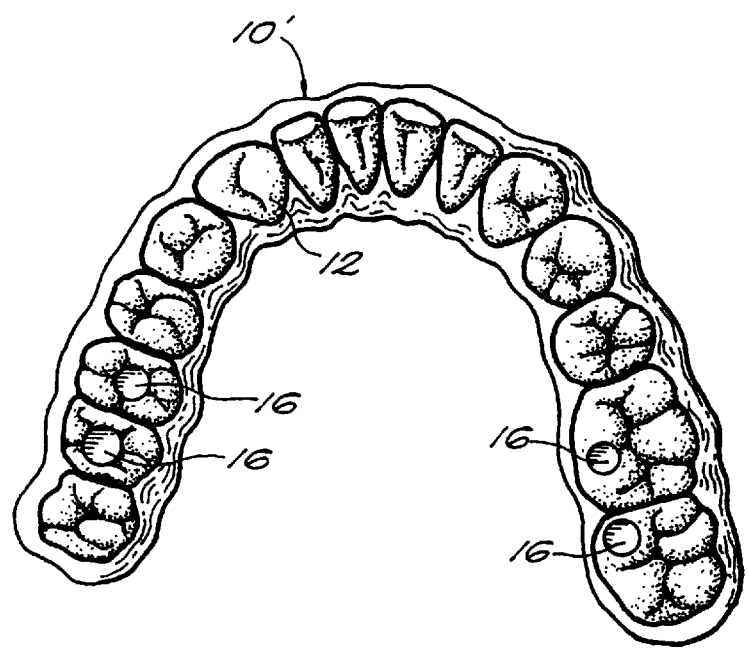
FIG. 3 depicts an overhead view of a stent revealing tooth-shaped molds which conform to a patient's teeth and guide holes for orienting and placing implants.

Referring to FIG. 3, an overhead view of a stent 10' is depicted revealing a plurality tooth-shaped molds which conform to a patient's teeth and a plurality of guide holes 16. Guide holes 16 are positioned based on radiographs showing the density and mass of the bone of the underlying mandible. Further, guide holes 16 are used to guide drilling tools (not shown) and to orient implants (not shown) on which restorations (not shown) may be mounted.

Figure 4:
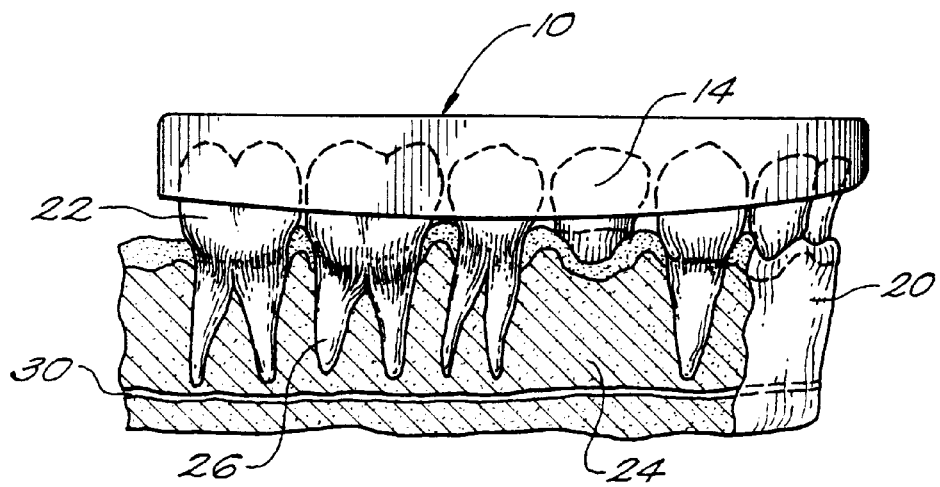
FIG. 4 depicts the stent and restoration of FIG. 1 mounted on a patient's teeth. Portions of the gums and mandible have been cut-away to reveal the tooth roots and the supporting nerve.
Figure 5:
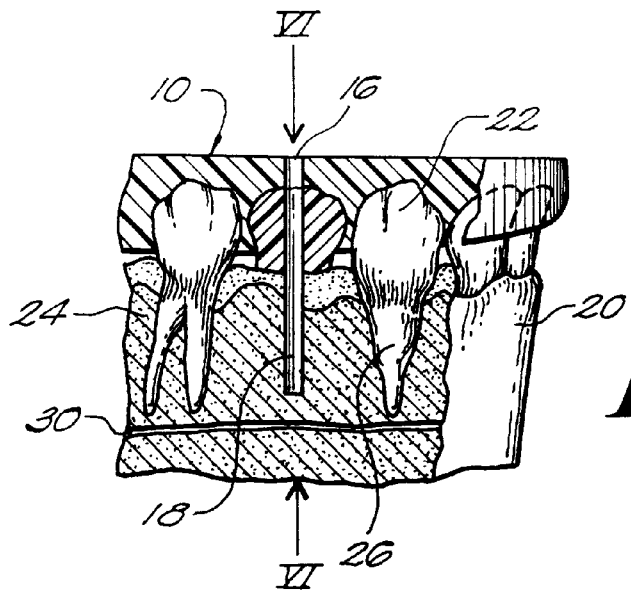
FIG. 5 depicts portions of the stent, restoration, teeth, gums, mandible, and supporting nerve of FIG. 4 with the addition of a guide hole and an implant fixed in the mandible.
Figure 6:
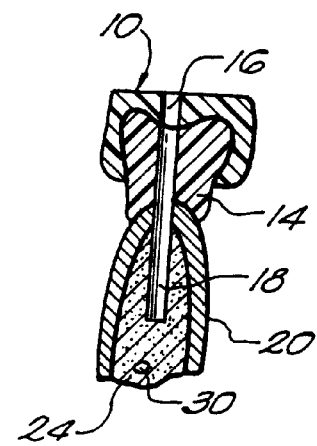
FIG. 6 depicts a cross-sectional view of the implant of FIG. 5 along the Line VI—VI.

FIG. 4 depicts stent 10 and restoration 14 of FIG. 1 mounted on the patient's teeth 22. As may be seen from this figure, the plurality of tooth-shaped molds 12 conform to and receive teeth 22. Portions of gums 20 and mandible 24 have been cut-away to reveal the tooth roots 26 and a supporting nerve 30. Moreover, in FIG. 5, portions of stent 10, restoration 14, gums 20, teeth 22, mandible 24, and supporting nerve 30 of FIG. 4 with the addition of a guide hole 16 and an implant 18 in the form of a screwed-in-post, which is fixed in mandible 24. Restoration 14 may then be mounted on implant 18. Referring to FIG. 6, a cross-sectional view of implant 18 and restoration 14 is shown along the Line VI—VI of FIG. 5.

The invention may be further clarified by consideration of the following examples, which are intended to be purely exemplary of the use of the invention. Further, the unexpected results revealed by the following tests are exemplary of the performance of embodiments of the process and paint of the present invention.

EXAMPLES

The process described above was used to prepare a water-soluble, radio-opaque paint for marking radio-lucent dental stents. The process included the steps of preparing a solution comprising 50 ml of ethanol; 6.4 grams of glycerol; 4.0 ml of benzaldehyde; 1.0 ml of glacial acetic acid, and 0.15 grams of hydroxy propyl cellulose. A radio-opaque powder, including 50 grams of barium sulfate with a mean particle diameter of about 10 $\mu$m, then is added to the solution. The solution is then mixed using ultrasound, for example, sound with a frequency of about 20,000 cpm, to obtain the paint having a uniform dispersion of the radio-opaque powder.

This paint was then applied to a dental stent, and the stent is placed on a patient's teeth. A radiographic image was taken of the stent and the patient's teeth. If the radiographic image of the stent was too faint, e.g., if the outline and boundaries of the stent were not clear, additional paint was applied to the stent, as needed. A first radiograph may be used as a guide for the application of additional paint. Additional applications then were applied if additional radiographs indicate further applications are required. The stent then is removed from the patient's teeth, and the paint is removed from the stent.

Figure 7:
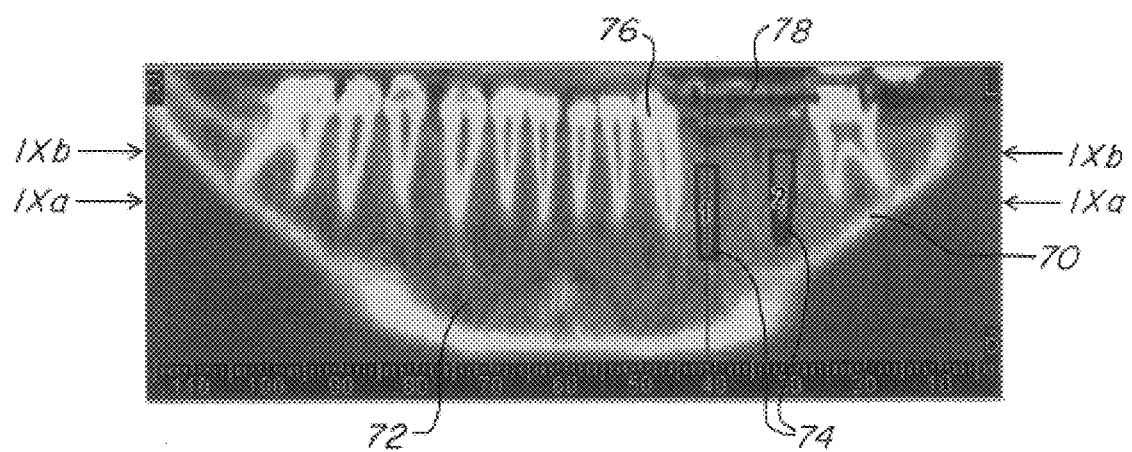
FIG. 7 is a frontal view radiograph of a patient's mandible and mandibular teeth with a stent painted in accordance with the invention.
Figures 8A, 8B, 8C:
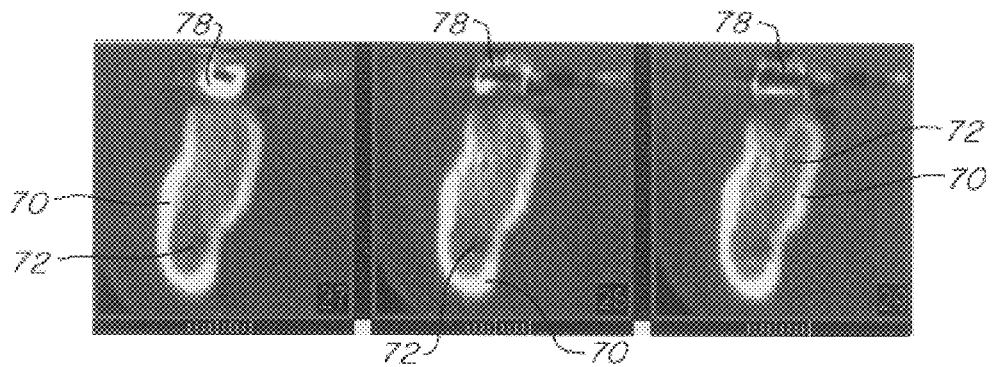
FIGS. 8a–i are successive cross-sectional views of the location of an implant in the patient's mandible of FIG. 7 taken along lines substantially perpendicular to Line IXa—IXa and Line IXb—IXb.
Figures 8D, 8E, 8F:
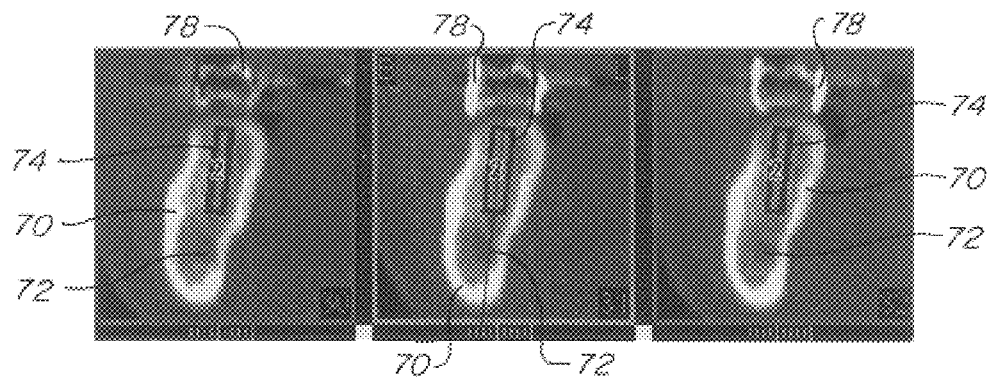
Figures 8G, 8H, 8I:
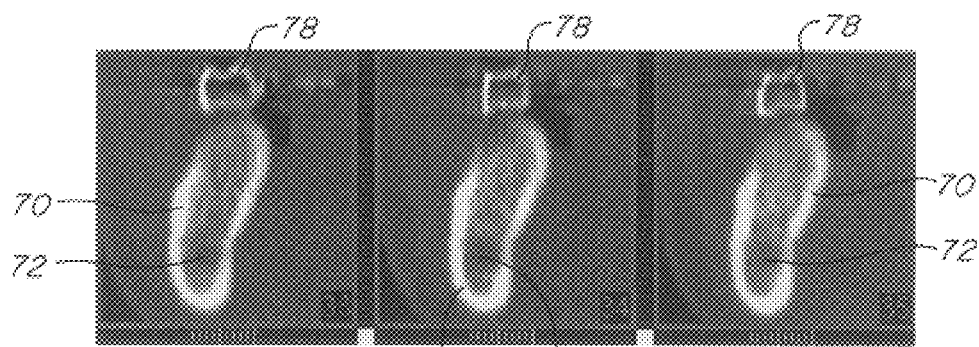

Referring to FIG. 7, a frontal view radiograph of a first patient's mandible and mandibular teeth with a stent painted in accordance with the invention is depicted. The dense cortical bone plate 70 appears as the white outline of the mandible. Cortical bone plate 70 is denser and more radio-opaque than the medullary bone 72 which appears as the somewhat fuzzy or less dense structure within the cortical bone plate 70. Natural teeth 76 are dense and, like cortical bone plate 70, generally radio-opaque. However, soft tissue, such as tooth pulp, nerves, and gum tissue, and the like, is radio-lucent.

This radiograph was generated using SIM/Plant® software, commercially available from Columbia Scientific Inc. of Columbia, Md., U.S.A. SIM/Plant® software is a Windows-based computer program that allows a dentist, oral surgeon, periodontist, or the like, to simulate the placement of various lengths, diameters, and styles of implants, e.g., screw-in-posts, such as simulated implants 74, the characteristics of which are entered into the computer. Further, stent 78 corresponds to the patient's teeth 76, but its outline appears in the gap in the teeth above simulated implants 74, i.e., implants #1 and #2. Through the use of this software, the dentist, oral surgeon, periodontist, or the like, is able to simulate the use of various sizes and styles of implants in a particular patient. Before the implant is placed, the appropriate size and style of implant may be selected for use in the existing bone foundation.

FIGS. 8a–i are successive cross-sectional views of the location of simulated implant 74, i.e., implant #2, in the patient's mandible of FIG. 7 taken along lines substantially perpendicular to Lines IXa—IXa and Lines IXb—IXb. Each view is taken at one millimeter intervals with the buccal aspect of the patient's mandible on the left side of each view and the lingual aspect of the patient's mandible on the left side of each view. The buccal and lingual aspects of cortical bone plate 70 of the mandible are shown in each view, and vertical cross-sections of stent 78 are visible above the level of the mandible's medullary bone 72.

Figure 9A:
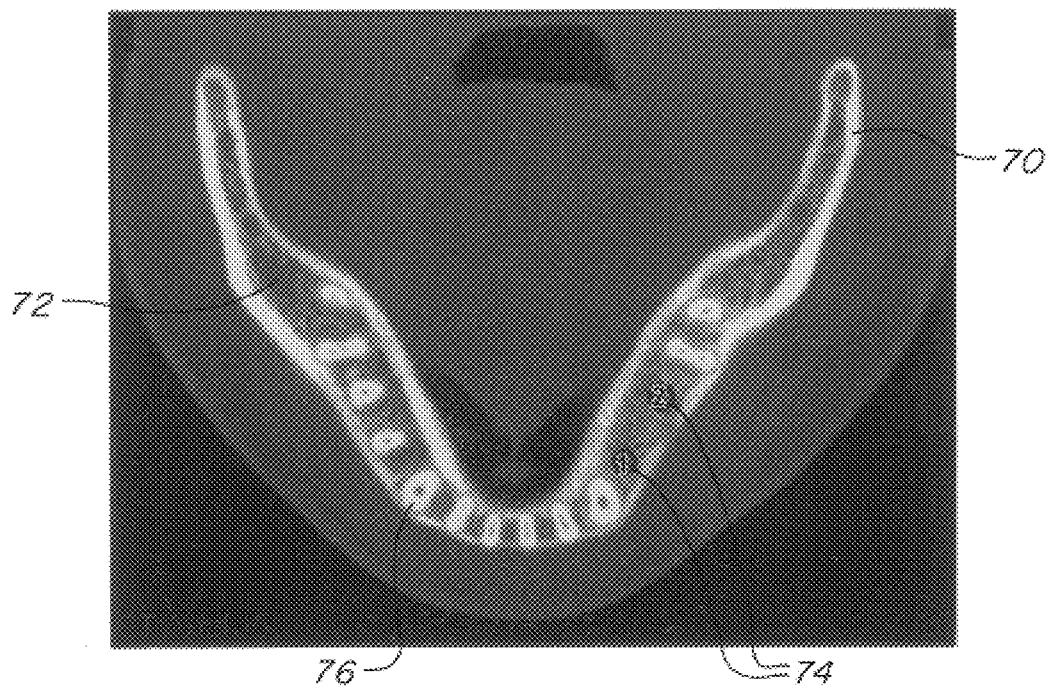
FIG. 9a is a cross-sectional (or sagittal) view of the patient's mandible of FIG. 7 along the Line IXa—IXa.
Figure 9B:
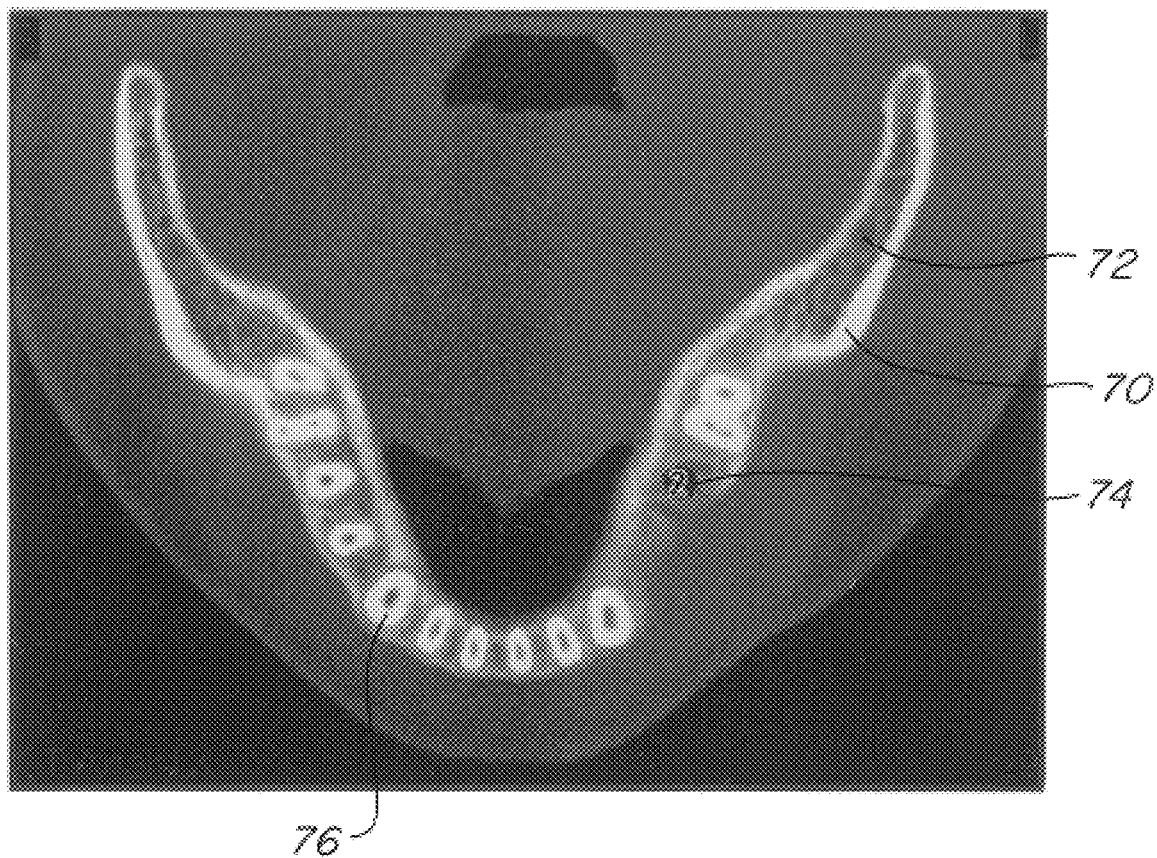

FIG. 9a is a cross-sectional view of the patient's mandible of FIG. 7 along the Line IXa—IXa. FIG. 9b is a cross-sectional view of the patient's mandible of FIG. 7, taken above the cross-sectional view depicted in FIG. 9a along the Line IXb—IXb. Unlike FIG. 9a, only one of the simulated implants 74 is depicted in FIG. 9b.

Figure 10B:
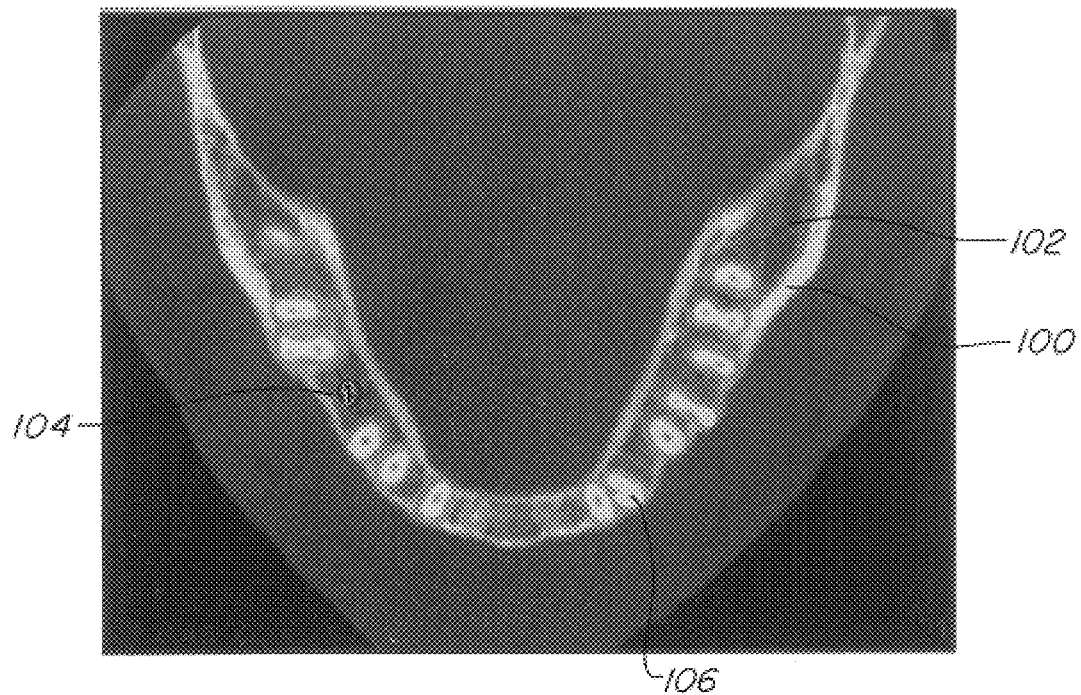
FIG. 10b is a cross-sectional view of the patient's mandible of FIG. 10a along the Line Xb—Xb.
Figure 10A:
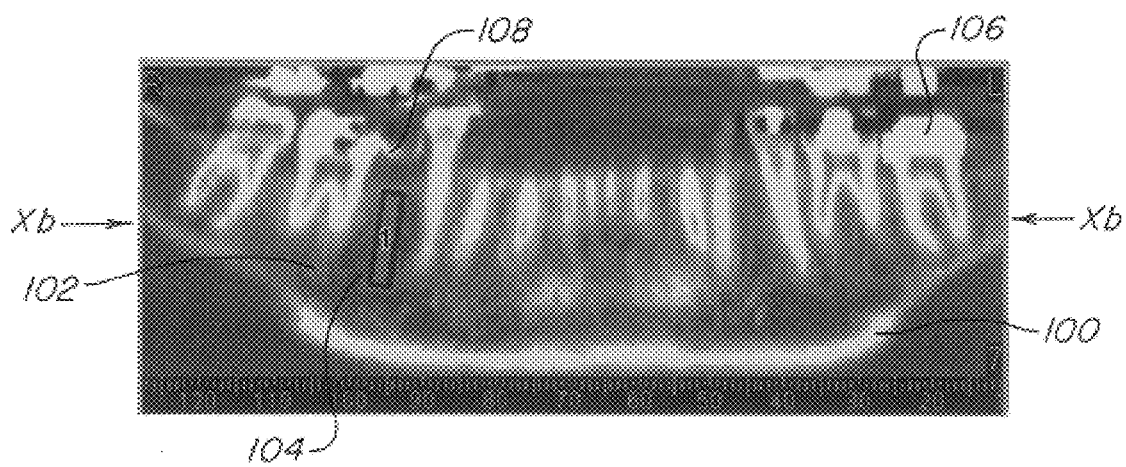
FIG. 10a is a frontal view radiograph of a patient's mandible and mandibular teeth with a stent painted in accordance with the invention.
Figures 11A, 11B, 11C:
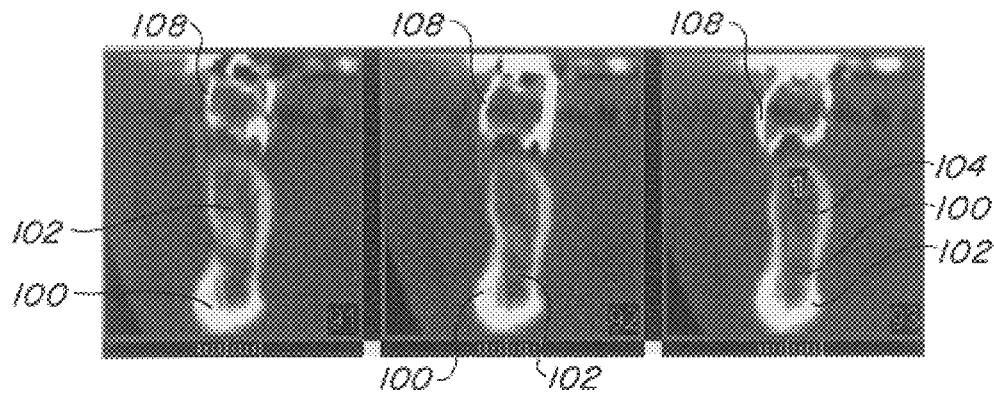
FIGS. 11a–i are successive cross-sectional views of the location of an implant in the patient's mandible of FIG. 10a taken along lines substantially perpendicular to Line Xb—Xb.
Figures 11D, 11E, 11F:
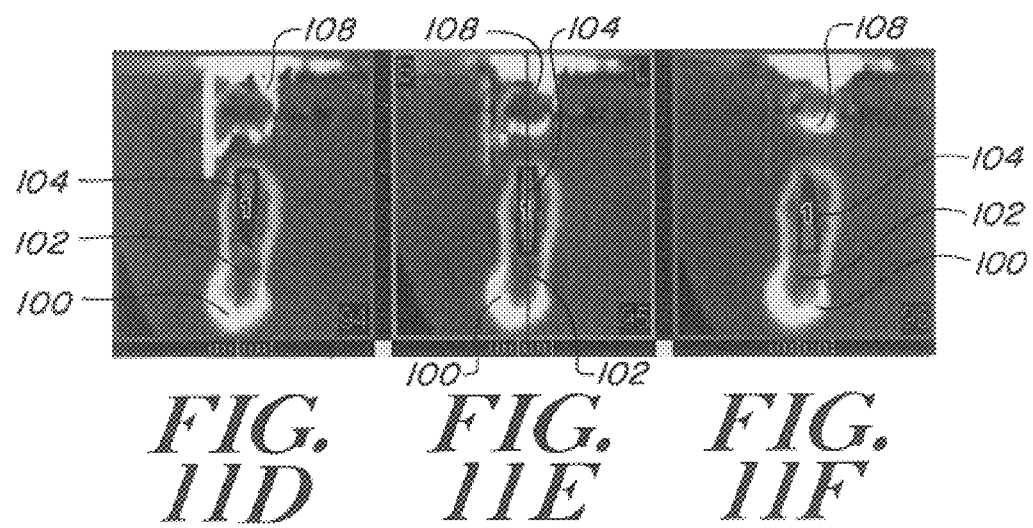
Figures 11G, 11H, 11I:
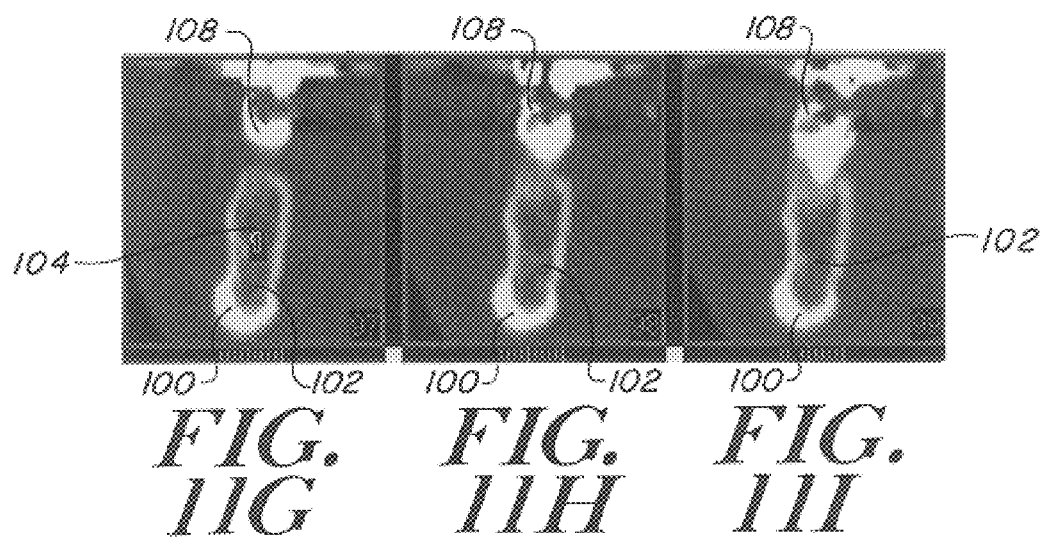

Referring to FIG. 10a, a frontal view radiograph of a second patient's mandible and mandibular teeth with a stent painted in accordance with the invention is depicted. The dense cortical bone plate 100 appears as the white outline of the mandible. Cortical bone plate 100 is denser and more radio-opaque than the medullary bone 102 which again appears as the fuzzy or less dense structure within the cortical bone plate 100. Natural teeth 106 are dense and, like cortical bone plate 100, generally radio-opaque. However, soft tissue, such as tooth pulp, nerves, gum tissue, and the like, is radio-lucent. Further, stent 108 corresponds to the patient's teeth 106, but its outline appears in the gap in the teeth above simulated implant 104, e, implant #1. FIG. 10*b* is a cross-sectional view of the patient's mandible of FIG. 10*a* along the Line Xb—Xb.

FIGS. 11*a–i* are successive cross-sectional views of the location of simulated implant 74 in the patient's mandible of FIG. 10*a* taken along lines substantially perpendicular to Lines IXa—IXa and Lines IXb—IXb. Each view is taken at one millimeter intervals with the buccal aspect of the patient's mandible on the left side of each view and the lingual aspect of the patient's mandible on the left side of each view. The buccal and lingual aspects of cortical bone plate 100 of the mandible are shown in each view, and vertical cross-sections of stent 108 are visible above the level of the mandible's medullary bone 102.

Other embodiments of the invention will be apparent to the skilled in the art from a consideration of this specification or practice of the invention disclosed herein. It is intended that the specification and examples be considered as exemplary only.

We claim:

1. A process for preparing a water-soluble, radio-opaque paint for coating or marking medical stents comprising the steps of:

preparing a solution comprising a polar solvent, a liquid adhesion thickener, a preservative, a food grade acidulant, and a dispersion stabilizer;

adding a radio-opaque powder to said solution; and sonifying said solution with ultrasound to obtain said paint, wherein said paint has a homogenous dispersion of said radio-opaque powder so as to be uniformly radio-opaque, wherein said food grade acidulant consists of an acid selected from the group consisting of acetic acid, benzoic acid, citric acid, formic acid, lactic acid, malic acid, phosphoric acid, and tartaric acid.

2. The process of claim 1, wherein said solvent comprises about 50 ml of ethanol.

3. A. The process of claim 1, wherein said liquid adhesion thickener comprises about 6.4 grams of glycerol.

4. The process of claim 1, wherein said preservative comprises about 4 ml of benzaldehyde.

5. The process of claim 1, wherein said dispersion stabilizer comprises about 0.15 grams of hydroxy propyl cellulose.

6. The process of claim 1, wherein said food grade acidulant comprises about 1 ml of glacial acetic acid.

7. The process of claim 1, wherein said radio-opaque powder comprises about 50 grams of barium sulfate powder having a mean particle diameter of less than about 10 $\mu$m.

8. A process for preparing a water-soluble, radio-opaque paint for coating or marking medical stents comprising the steps of:

preparing a solution comprising about 50 ml of ethanol, about 6.4 grams of glycerol, about 4 ml of benzaldehyde, about 1 ml of glacial acetic acid, and about 0.15 grams of hydroxy propyl cellulose;

adding about 50 grams of barium sulfate powder having a mean particle diameter of less than about 10 $\mu$m to said solution; and sonifying said solution with ultrasound to obtain said paint, wherein said paint has a uniform dispersion of said barium sulfate powder.

9. A water-soluble, radio-opaque paint consisting essentially of a polar solvent, a liquid adhesion thickener, a preservative, a food grade acidulant, a dispersion stabilizer, and a radio-opaque powder.

10. The paint of claim 9, wherein said solvent comprises about 50 ml of ethanol.

11. The paint of claim 9, wherein said liquid adhesion thickener comprises about 6.4 grams of glycerol.

12. The paint of claim 9, wherein said preservative comprises about 4 ml of benzaldehyde.

13. The paint of claim 9, wherein said dispersion stabilizer comprises about 0.15 grams of hydroxy propyl cellulose.

14. The paint of claim 9, wherein said food grade acidulant consists of an acid selected from the group consisting of acetic acid, benzoic acid, citric acid, formic acid, lactic acid, malic acid, phosphoric acid, and tartaric acid.

15. The paint of claim 9, wherein said food grade acidulant comprises about 1 ml of glacial acetic acid.

16. The paint of claim 9, wherein said radio-opaque powder comprises about 50 grams of barium sulfate powder having a mean particle diameter of less than about 10 $\mu$m.

17. A water-soluble, radio-opaque paint comprising about 50 ml of ethanol, about 6.4 grams of glycerol, about 4 ml of benzaldehyde, about 1 ml of acetic acid, about 0.15 grams of hydroxy propyl cellulose, and about 50 grams of barium sulfate powder having a mean particle diameter of less than about 10 $\mu$m.

\* \* \* \* \*